United States Patent [19]
Tam

[11] Patent Number: 5,465,283
[45] Date of Patent: Nov. 7, 1995

[54] METHOD AND APPARATUS FOR GENERATING RADON DERIVATIVE DATA ON A NEAR UNIFORMLY SPACE GRID IN A CONE BEAM COMPUTERIZED TOMOGRAPHY IMPLEMENTATION

[75] Inventor: Kwok C. Tam, Schenectady, N.Y.

[73] Assignee: General Electric Company, Schenectady, N.Y.

[21] Appl. No.: 254,711

[22] Filed: Jun. 6, 1994

[51] Int. Cl.⁶ .............................. A61B 6/03; G01N 23/08
[52] U.S. Cl. .............................................. 378/4; 378/901
[58] Field of Search ........................................ 378/4, 901

[56] References Cited

U.S. PATENT DOCUMENTS 5,257,183  10/1993  Tam ..................................... 364/413.19
5,270,926  12/1993  Tam ..................................... 364/413.19
5,333,164   7/1994  Tam ............................................. 378/8
5,355,309  10/1994  Eberhard et al. .................. 364/413.15
5,365,560  11/1994  Tam ............................................. 378/8

OTHER PUBLICATIONS

"Image Reconstruction From Cone-Beam Projections: Necessary and Sufficient Conditions and Reconstruction Methods" by Bruce D. Smith, IEEE Trans on Medical Imaging, vol. MI-4, No. 1, Mar. 1985, pp. 14–25.

Primary Examiner—David P. Porta
Assistant Examiner—David Vernon Bruce
Attorney, Agent, or Firm—David C. Goldman; Paul R. Webb, II

[57] ABSTRACT

The present invention discloses a method and apparatus for generating Radon derivative data on locations proximate to a near uniformly spaced polar grid in a digitized Radon space for a cone beam computerized tomography (CT) implementation. Radon derivative data is determined for uniformly spaced coordinates in r, $\theta$ and $\phi$ directions.

16 Claims, 10 Drawing Sheets

5,465,283

METHOD AND APPARATUS FOR GENERATING RADON DERIVATIVE DATA ON A NEAR UNIFORMLY SPACE GRID IN A CONE BEAM COMPUTERIZED TOMOGRAPHY IMPLEMENTATION

BACKGROUND OF THE INVENTION

The present invention relates generally to three-dimensional (3D) computerized tomography (CT) and more particularly to the generation of Radon derivative data on a near uniformly spaced polar grid in a digitized Radon space.

In conventional CT for both medical and industrial applications, an x-ray fan beam and a linear array detector are used to achieve two-dimensional (2D) imaging. While the data set may be complete and image quality is correspondingly high, only a single slice of an object can be imaged at a time. Therefore, when a 3D image is required, a stack of 2D slices approach is employed. Acquiring a 3D data set, one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body.

In order to overcome the problems associated with the x-ray fan beam and linear array detector configuration, a cone beam x-ray source and a 2D array detector are used. With the cone beam x-ray source and linear array detector, the scanning is much faster than the slice-by-slice scanning of the fan beam. Also, since each "point" in the object is viewed by the x-rays in 3D rather than in 2D, a much higher contrast can be achieved than is possible with the conventional 2D x-ray CT. To acquire cone beam projection data in the cone-beam CT implementation, an object is scanned, preferably over a 360° angular range, either by moving the cone beam x-ray source in a scanning circle about the object, while keeping the 2D array detector fixed with reference to the cone beam x-ray source or by rotating the object while the x-ray source and detector remain stationary. The image of the object can be reconstructed by using a Radon inversion process, in which the total Radon transform of the cone beam projection data is computed. Computing the total Radon transform in the continuum Radon space requires a large amount of processing power and an infinite amount of time. In order to overcome this computing problem, the cone beam projection data is sampled so that the Radon transform is computed for a finite set of uniformly spaced points. The best results occur by sampling the Radon space into a polar grid having a plurality of uniformly spaced grid points. In a discrete Radon space, it is desirable to compute Radon derivative data on each of the uniformly spaced grid points. However, in order to compute Radon derivative data on each of the uniformly spaced grid points, there has to be a continuum of source positions located on the scanning trajectory. In practice, there is only a finite number of source positions and not a continuum of source positions. Thus, Radon derivative data cannot be precisely computed on each of the uniformly spaced grid points.

SUMMARY OF THE INVENTION

Therefore, it is a primary objective of the present invention to generate Radon derivative data on locations as dose as possible to each of the uniformly spaced grid points in the digitized Radon space for a cone beam CT implementation.

Thus, in accordance with the present invention, there is provided a method of generating Radon derivative data for cone beam energy emitted from a cone beam x-ray source passing through an object onto a detector. The method comprises providing a scanning trajectory about the object. The scanning trajectory is discretely sampled with a plurality of uniformly spaced cone beam source positions. Cone beam energy is emitted towards the object from each of the plurality of uniformly spaced cone beam source positions. The cone beam energy passes through the object and is acquired on the detector as cone beam projection data. The cone beam projection data is used to compute the Radon derivative. The Radon space is then partitioned into a plurality of co-axial vertical planes each having a polar grid with a plurality of polar grid points uniformly spaced in r, θ, and φ coordinates. Radon derivative data is then determined on locations proximate to each of the plurality of polar grid points for each of the co-axial vertical planes.

While the present invention will hereinafter be described in connection with a preferred embodiment and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
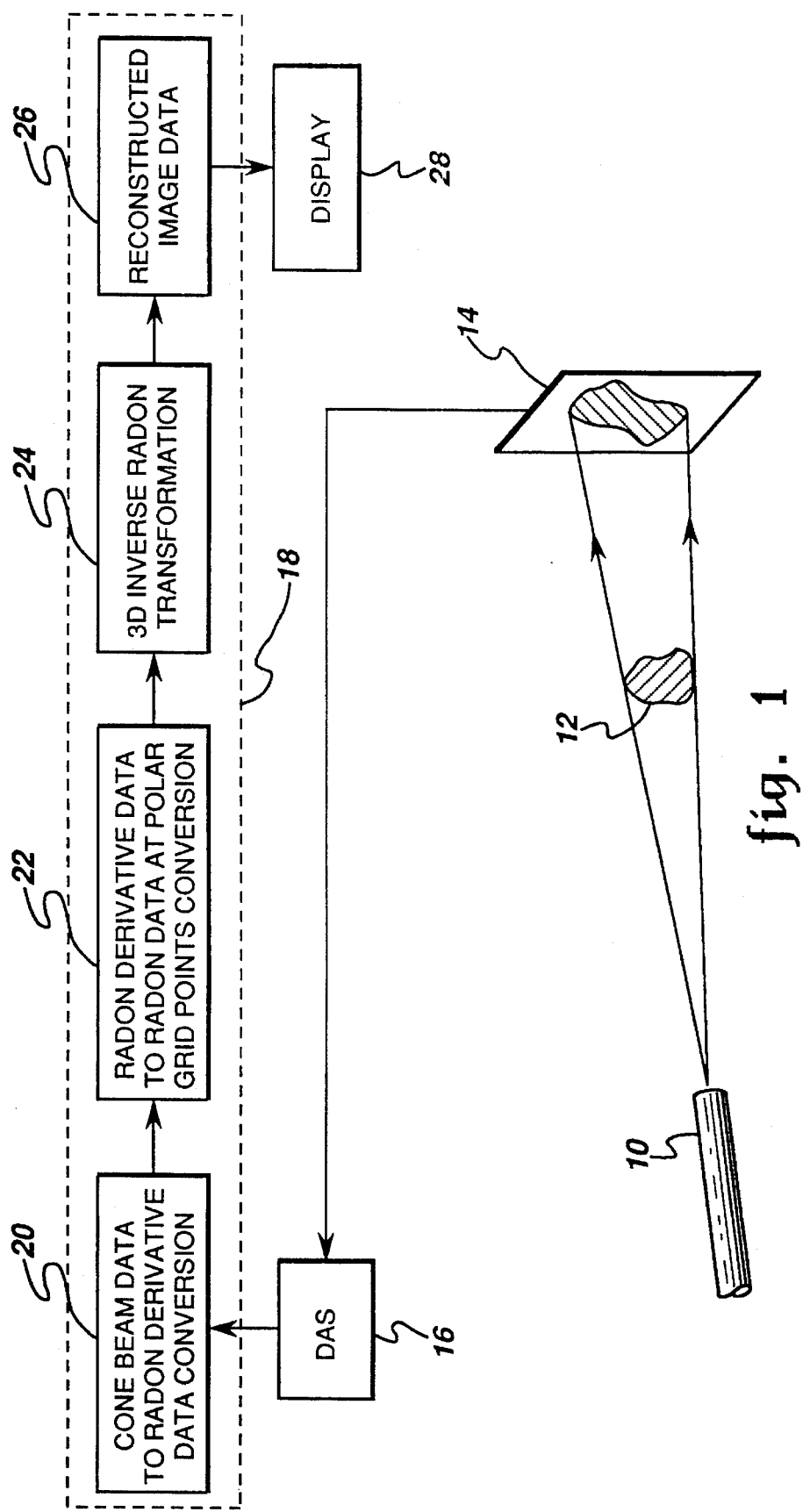
FIG. 1 is a perspective view of a cone beam CT system.

In FIG. 1, cone beam energy is emitted from a cone beam x-ray source 10 and passed through an object 12. The cone beam energy passing through the object is detected by a 2D array detector 14 which comprises an array of individual detector elements. Complete information is obtained by moving the cone beam x-ray source 10 and the detector 14 in relation to the object 12. For example, the object can be rotated about a vertical axis with respect to the x-ray source and the detector or the object can remain stationary while the source and detector are rotated about the object. Cone beam energy that penetrates the object is detected by the detector as cone beam projection data. The cone beam projection data is converted to corresponding electrical signals and sent to a data acquisition unit 16 which registers the electrical signals. The electrical signals corresponding to the cone beam projection data in the data acquisition unit are then sent to a processor 18, which may be a computer programmed to perform various data conversions. In particular, the cone beam projection data is converted to Radon derivative data at block 20 using the techniques described in the U.S. Pat. No. 5,257,183, which is incorporated herein by reference, and by using the techniques described later in the present invention. The Radon derivative data is then converted to Radon data at block 22 using the technique described in commonly assigned U.S. patent application Ser. No. 08/100,818, which is incorporated herein by reference. The Radon data at the polar grid points is then supplied to block 24 which performs an inverse 3D Radon transformation using the techniques described in detail in commonly assigned U.S. patent application Ser. No. 07/631,818, now abandoned, which is incorporated herein by reference. After the 3D inverse Radon transformation, reconstructed image data is obtained at block 26. The reconstructed image data is then fed from the processor 18 to a display 28, which provides a 3D CT image of the object 12.

Figure 2:
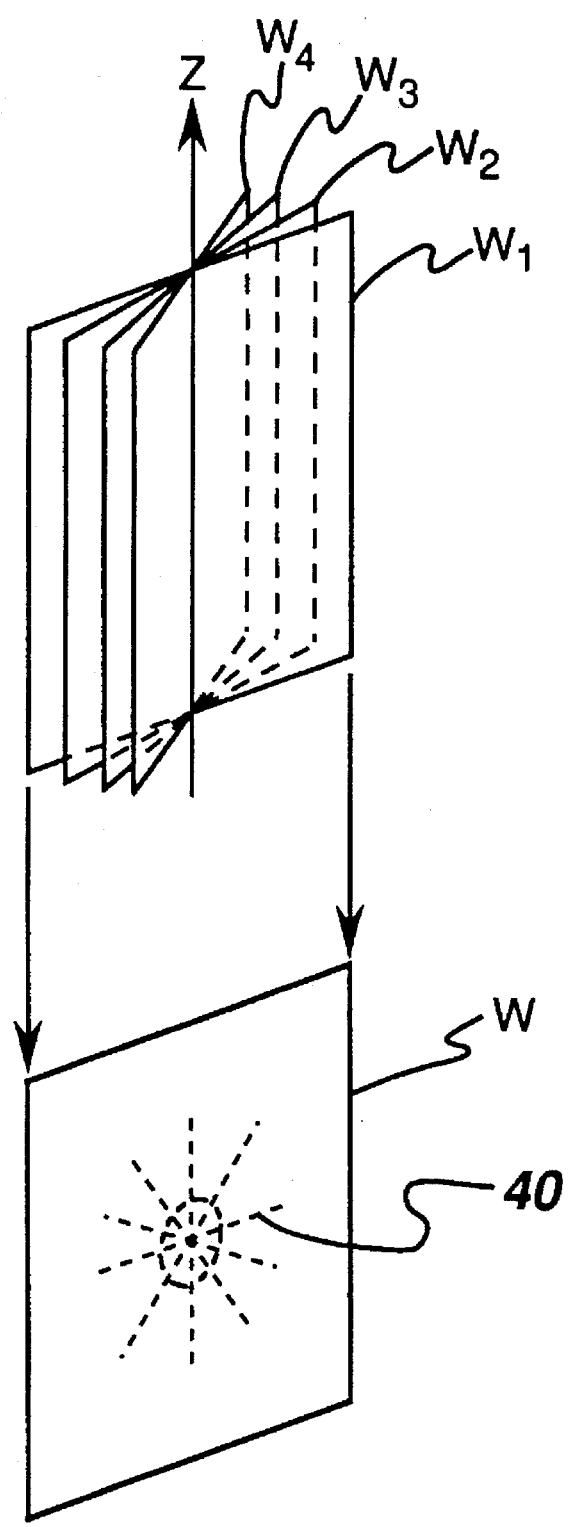
FIG. 2 shows a set of co-axial vertical planes in Radon space.

As explained in detail in U.S. Pat. No. 5,257,183, the Radon space of the object of interest 12 is partitioned into a number of vertical co-axial planes $W_1$-$W_n$ disposed about the z-axis as shown in FIG. 2. The planes extend at uniform angle separations completely around the z axis. For example, there could be 90 such planes, each separated from adjacent planes by 2°, extending on two sides of the z axis. Each vertical plane is partitioned into a uniformly spaced polar grid 40. As mentioned earlier, the Radon derivative data is determined on each of the polar grid points in each vertical plane so that a 2D projection image is reconstructed.

Figure 3:
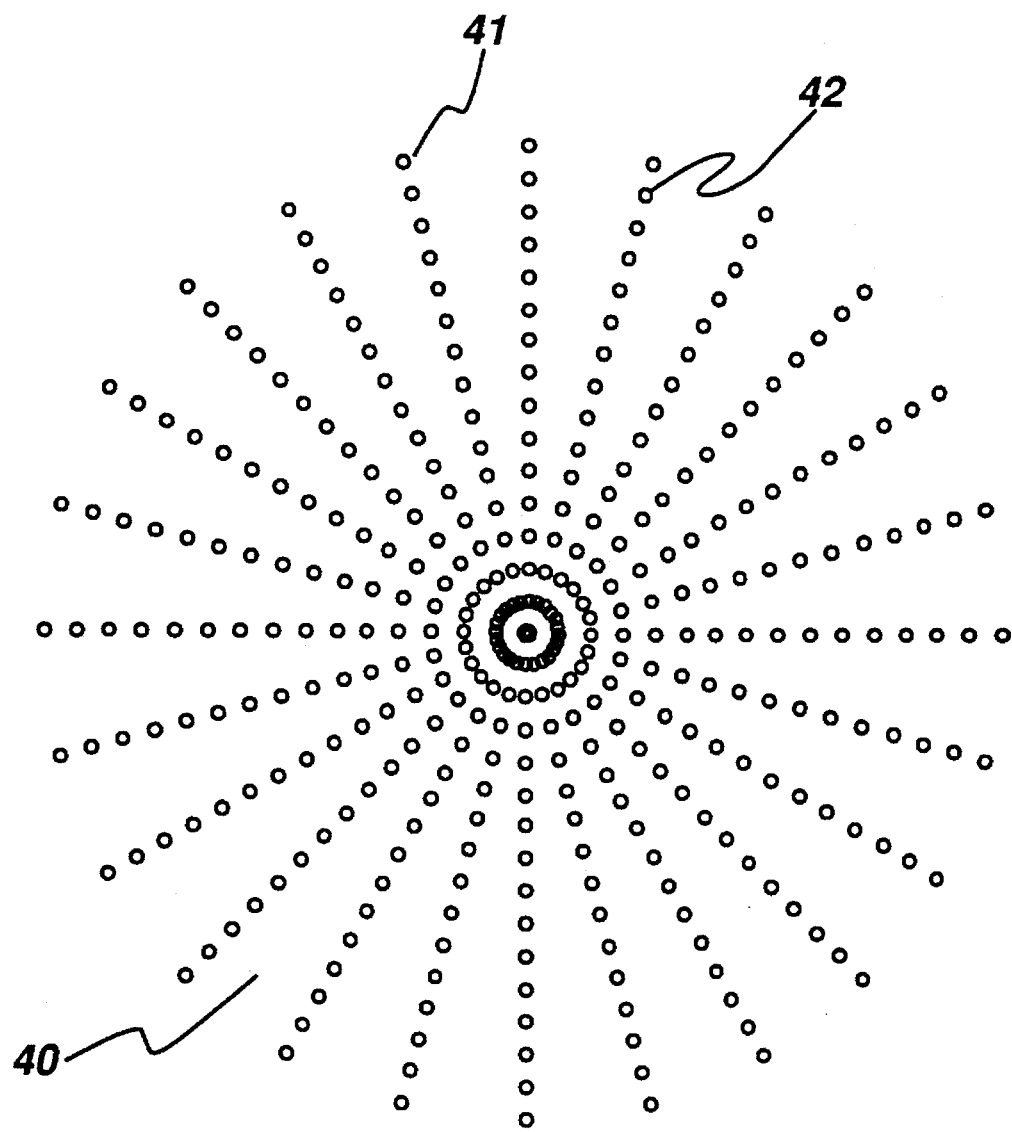
FIG. 3; is a plot of a uniformly spaced polar grid on a vertical plane.

The polar grid 40 is shown in further detail in FIG. 3. The polar grid includes a plurality of grid lines 42 each having a plurality of grid points 44 uniformly spaced in the r, θ, and φ coordinates. In order to meet the sampling criteria necessary for computing the inverse Radon transformation, it is preferable to generate Radon derivative data directly on each of the polar grid points. However, because the number of cone beam source positions in a typical scanning trajectory are finite, the Radon derivative data can only be calculated in a restricted range of points in the Radon space and these points may in general not fall exactly on the polar grid points.

Figure 4:
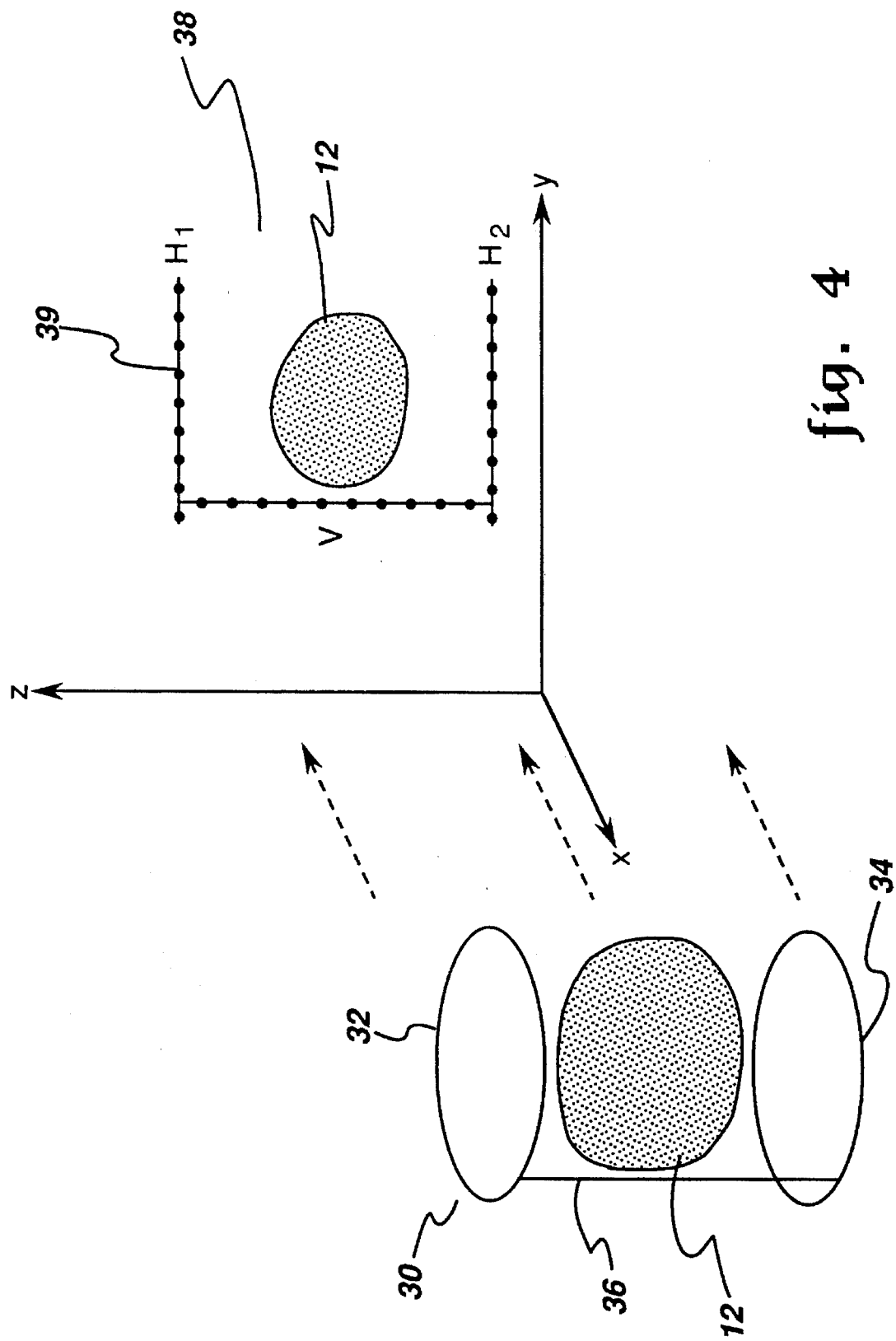
FIG. 4 illustrates a planar projection of a 3D scanning trajectory.

This problem is illustrated in a commonly adopted scanning trajectory as shown in FIG. 4. In this embodiment, the scanning trajectory 30 comprises two circular scan paths 32 and 34 and a connecting linear scan path 36. The scanning trajectory 30 is projected onto a plane, herein taken for convenience to be the yz plane, and identified as a projected planar scanning trajectory 38 comprising two horizontal lines $H_1$ and $H_2$ and a vertical line V, each comprising a plurality of source positions 39. The horizontal lines $H_1$ and $H_2$ correspond to scan paths 32 and 34, respectively, and the vertical line V corresponds to scan path 36. Note that the 3D object 12 being scanned is also shown projected onto the yz plane as a planar projection of the object.

Figure 5:
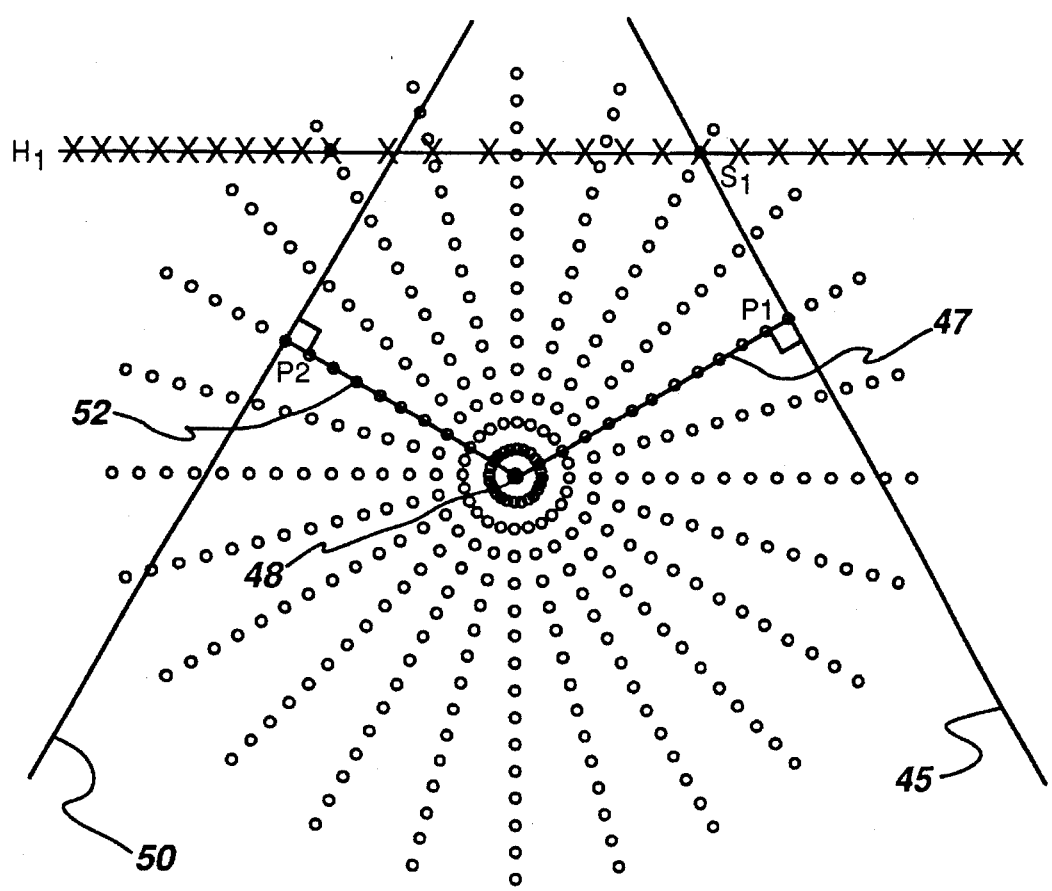
FIG. 5 is a plot of a uniformly spaced polar grid on a vertical plane for the 3D scanning trajectory of FIG. 4.

A polar grid of the 2planar projection shown in FIG. 4 is illustrated in FIG. 5. The Radon derivative at grid point P1 on the projection plane is due to cone beams generated from a source position S1 on $H_1$, traversing line 45 which represents the intersection of the projection plane with a surface orthogonal to a line segment 47 joining P1 and the origin 48. However, a Radon derivative value cannot be computed precisely at all grid points if the traversing line does not intersect a source position on either $H_1$ or $H_2$ (note that $H_2$ is not shown). For example, the surface orthogonal 50 to the line segment 52 connecting the origin to a grid point P2 does not intersect a source position along the scanning trajectory $H_1$. Therefore, a complete Radon derivative cannot be precisely computed at P2.

Figure 6:
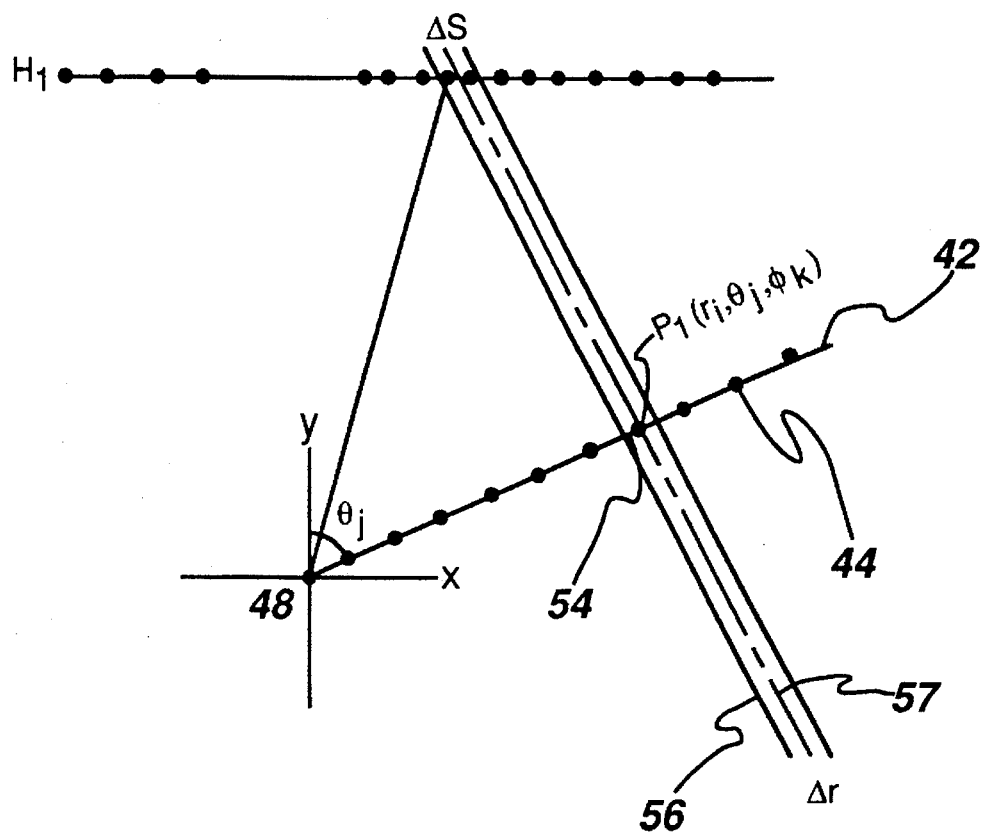
FIG. 6 is an illustration of a polar grid line and projected source positions on a vertical plane.

The present invention has solved this problem by generating Radon derivatives on locations as close as possible to each of the uniformly spaced grid points. In FIG. 6, the source positions 39 along the scanning trajectory $H_1$ ($H_2$ is not shown) are projected onto a vertical plane containing a uniformly spaced polar grid 40. However, to simplify the explanation of the present invention, only one polar grid line 42 with uniformly spaced grid points 44 in $\theta_j$ and $\phi_k$ are shown. Thus, each of the uniformly spaced grid points are separated by δr. As mentioned earlier, to determine the Radon derivative at a point P1 ($r_i$, $\theta_j$, $\phi_k$), a plane 57 perpendicular to the line connecting the origin 48 and P1 is used. If the perpendicular plane intersects at a source positions 39, then the Radon derivative can be computed. However, in FIG. 6, the perpendicular plane does not intersect a source position, and therefore the Radon derivative data cannot be precisely computed for point P1. In order to compute Radon derivative data as close as possible to the grid points, the present invention computes the Radon derivative within a bin or interval 54 from the grid point. Instead of using a perpendicular plane with zero width, a band 56 with a width Δr is used. A band with a width Δr ensures that a projected source position 39 will be intersected. The location of the Radon derivative data, or "hits", is generated by the source position at the intersection between the band and the projected source position line, and is characterized by the coordinates ($r_i$+δr, $\theta_j$, $\phi_k$), where $0 \leq r \leq \Delta r$ represents the uncertainty in the r coordinate of the hits.

In order to ensure that the band 56 always intersects a projected source position 39, the source positions on the scanning trajectory have to be aligned properly. The width of intersection ΔS is equal to Δr/sin$\theta_j$. If the source positions 39 are uniformly spaced on the scanning trajectories 32 and 34, then it is necessary to have the spacing between their projected positions on $H_1$ and $H_2$ small near the ends and large as the center is approached. Examination of FIG. 6 shows that the width of intersection ΔS reaches a minimum, equal to Δr, when the band 56 is vertical, intersecting $H_1$ or $H_2$ at x=0. If the band intersects $H_1$ or $H_2$ at x=0 when the band is vertical, then there is a "hit" at this location and for all locations where $\Delta S \geq \Delta r$. In this case, the minimum number of source positions $N_s$ that will ensure a "hit" is equal to 2πA/Δr, where A is the radius of the scan circle.

Figure 7:
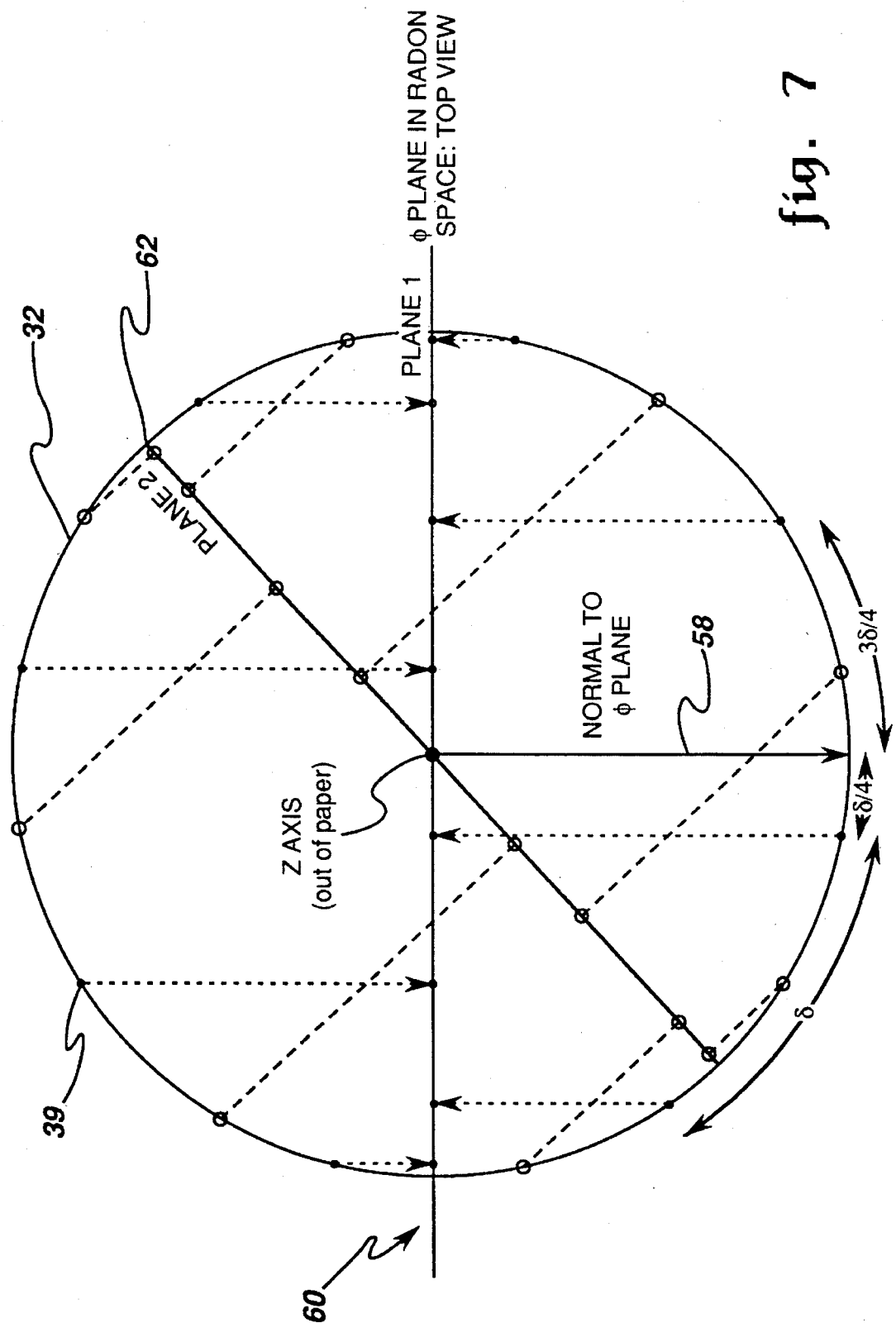
FIG. 7 is an illustration of sampling cone beam source positions along a scanning trajectory.

Since the projection of the scanning circles $H_1$ and $H_2$ are horizontal, the spacing between the source positions can be relaxed to twice the value specified above, so that $N_s$ equals 4πA/Δr. However, in order to use this criteria, the number of vertical planes in Radon space $N_i$ that receive the projected source positions have to be chosen such that the number of source positions $N_s$ is twice an integral multiple M of $N_i$ (i.e. $N_s$=2M$N_i$). In this case, the angular spacing between the planes is an integral multiple of the angular spacing between the number of source positions $N_s$. FIG. 7 illustrates an even number of cone beam source positions along a scanning trajectory. In FIG. 7, a normal 58 characterizes a first plane 60. It is displaced at angular spacings of δ/4 and 3δ/4, respectively from two adjacent source positions. This configuration minimizes the spacing of the projected source positions on the plane 60. The same conditions result for other vertical planes such as 62, if the criterion $N_s$= 2M$N_i$ is satisfied.

Figure 8:
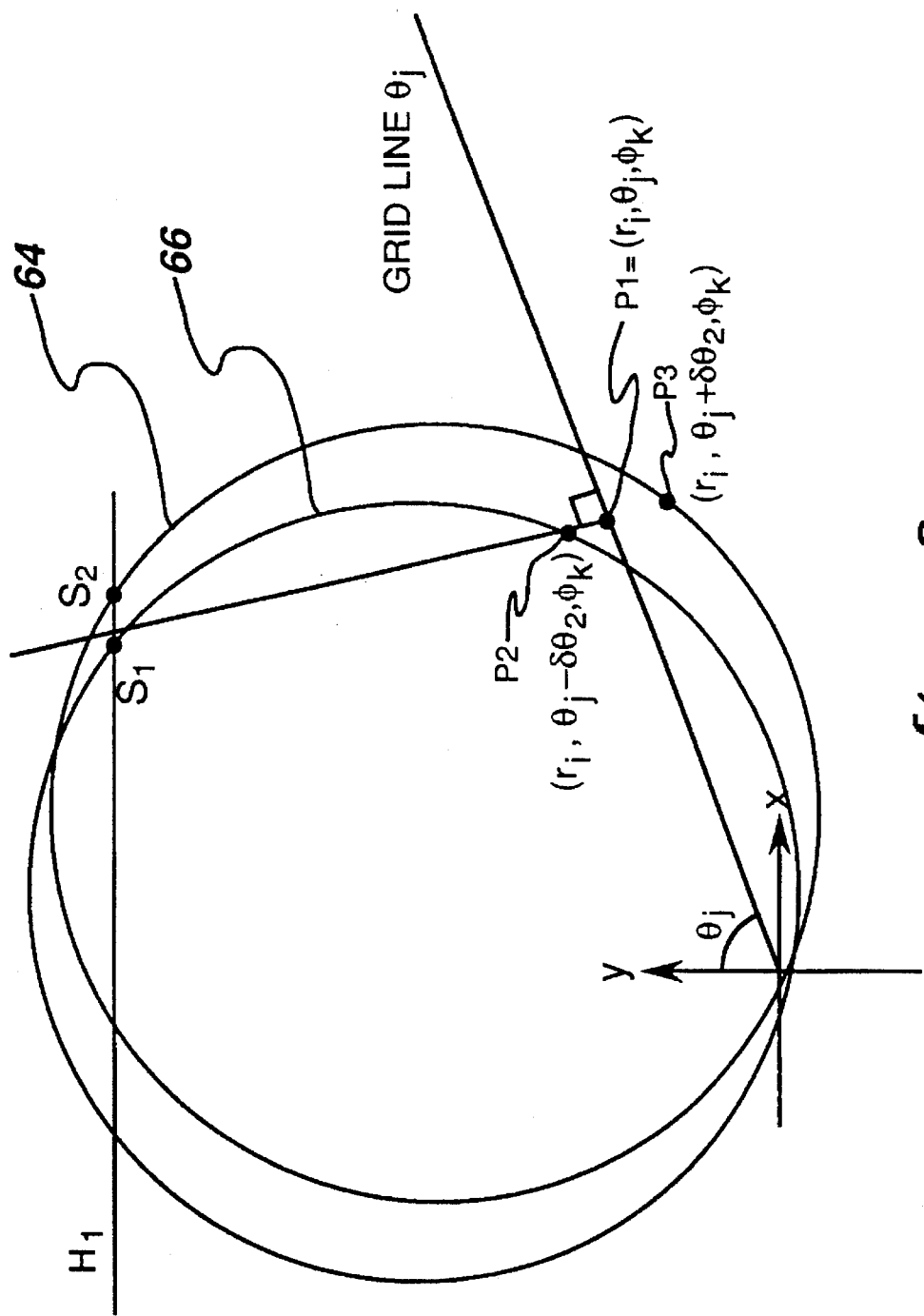
FIG. 8 is an illustration of a polar grid line and two Radon circles.

If the above-described source sampling interval results in in a miss for the polar grid shown in FIG. 6 because the number of source positions do not meet the minimum criterion (i.e. 2πA/Δr), then some of these empty intervals can be filled with "hits" by forming a first and second Radon circle 64 and 66, respectively, about the point P1 ($r_i$, $\theta_j$, and $\phi_k$) as shown in FIG. 8. In particular, the first and second Radon circles are each generated from the source positions (i.e. S1 and S2) that are adjacent to the band. The first and second Radon circles are separated by $\delta\theta$, wherein the first Radon circle 64 has a point P2 with coordinates ($r_i$, $\theta_j$–$\delta\theta_1$, $\phi_k$) and the second Radon circle 66 has a point P3 with coordinates ($r_i$, $\theta_j$+$\delta\theta_2$, $\phi_k$). A "hit" can be generated by computing the Radon derivative value for point P2 and point P3, and then interpolating the values to determine the Radon derivative value for point P1.

Figure 9A:
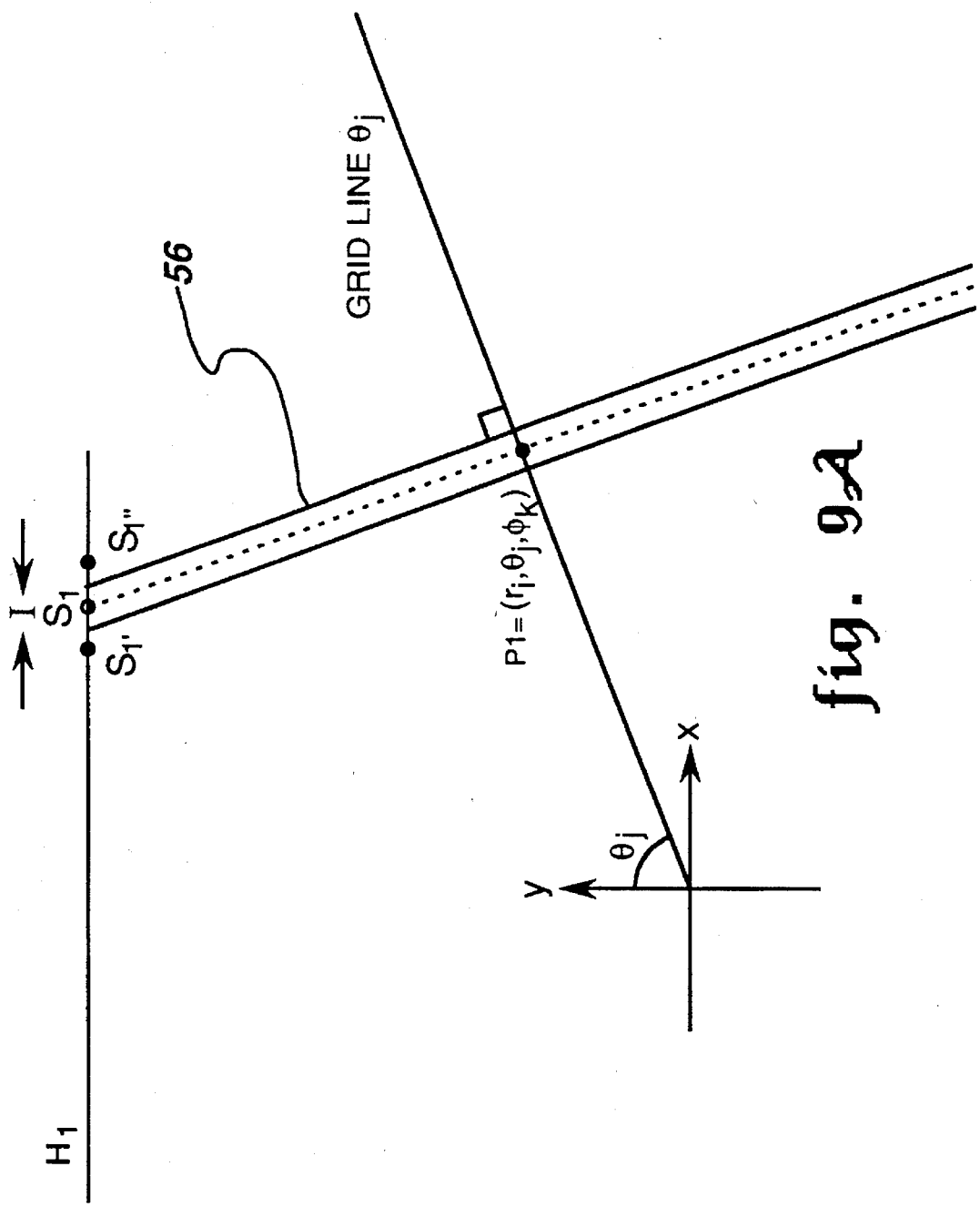
FIGS. 9a–9b are further illustrations of a polar grid line and projected source positions in a vertical plane.
Figure 9B:
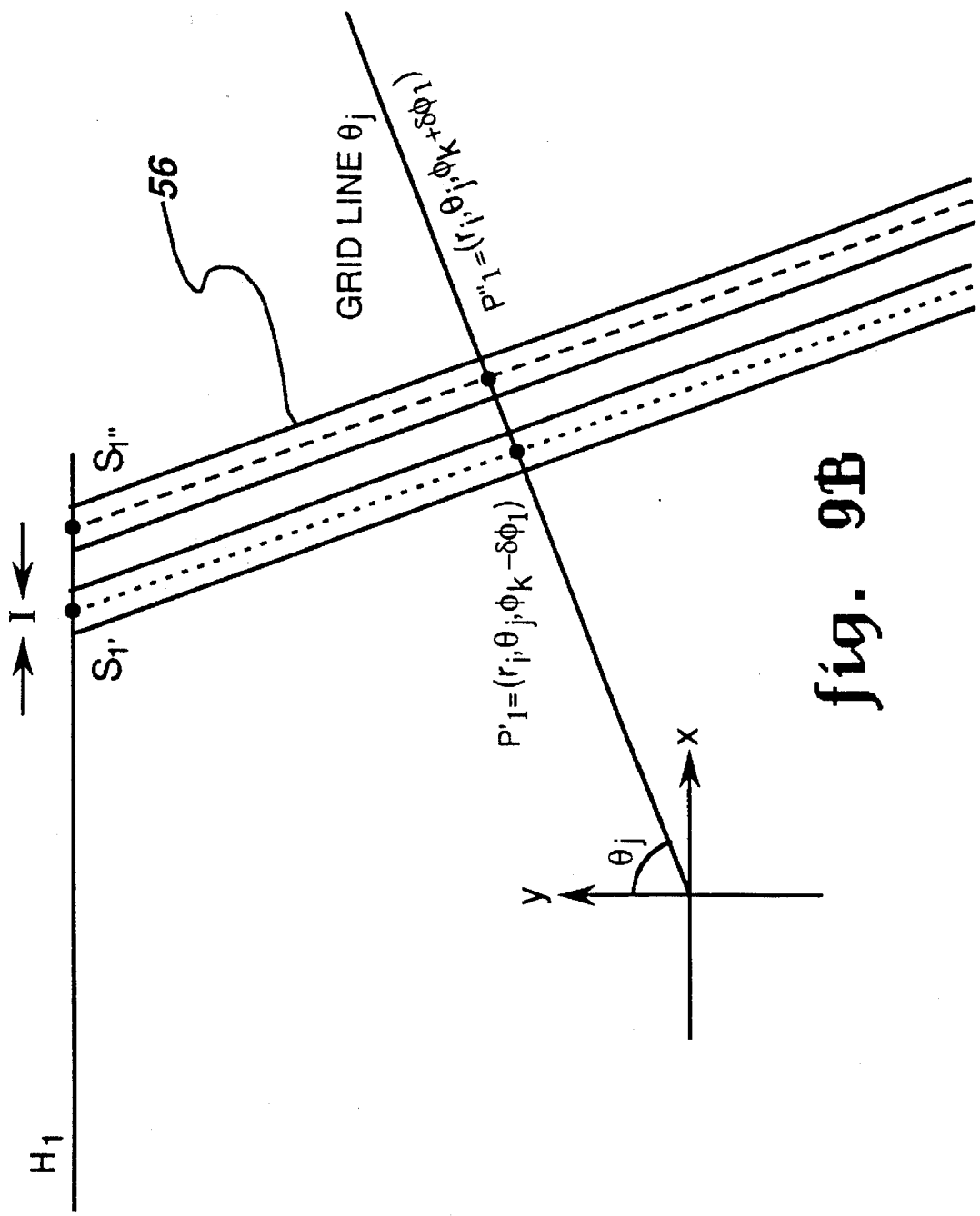

If the source sampling interval results in another miss, then these empty intervals can be filled with "hits" by examining coordinates of the type ($r_i$, $\theta_j$, $\phi_k$+$\delta\phi$). In FIG. 9a, the band 56 point P1 ($r_i$, $\theta_j$, and $\phi_k$) intersects $H_1$ at the interval I. Since the P1 interval is empty, there are no projected source positions in the interval I and thus there are no "hits", so a Radon derivative value cannot be computed at P1. If the interval did contain a source position S1, then there would be a "hit". However, a "hit" can be generated by computing Radon derivative data for adjacent projected cone beam source positions S1' and S1", wherein $0 \leq \delta\phi1$ is the difference between view angles of the source positions that project into S1 and S1' and $0 \leq \delta\phi2$ is the difference between view angles of the source positions that project into S1 and S1". In FIG. 9b, the vertical plane in Radon space is rotated from the $\phi_k$ plane about the z-axis by an amount $\delta\phi1$, so that the azimuthal angle of the plane is $\phi_k$–$\theta\phi1$ and the band 56 is shifted $\phi_k\theta\phi1$ so that the grid interval has a center point P1' equal to ($r_i$, $\theta_j$, $\phi_k$– $\delta\phi1$). The P1' interval intersects $H_1$ at projected cone beam source beam position S1'. Therefore, a "hit" occurs and a Radon derivative value is computed. Similarly, a grid interval with point P1" at its center can be derived so that it intersects the horizontal line $H_1$ at cone beam source position S1$\Delta$ by shifting the band $\phi_k$+$\delta\phi1$, resulting in a "hit". Then the Radon derivative values computed for points P1' and P1" are used to interpolate a Radon derivative value for point P1. Since S1 is sandwiched between the actual source positions S1' and S1", $\Delta\alpha \geq \delta\phi1$, $\delta\phi2$, where $\Delta\alpha$ is the view angle spacing. If the view angle spacing $\Delta\alpha$ is less than the vertical plane angle spacing $\Delta\phi$ in the 3D polar grid, then $\delta\phi1$, $\delta\phi2$ are $\leq \Delta\phi$. Since there are projected source positions on either side of any interval on $H_1$, an interval can always be filled in the polar grid via interpolation along $\phi$.

The steps described in detail with respect to FIGS. 6 and 8–9 are repeated for all of the polar grid points in the polar grid. Likewise, these steps are repeated for all of the polar grids defined in each of the vertical planes. As mentioned earlier, once the Radon derivative data is obtained for the polar grid points on the various vertical planes, the Radon derivative data is integrated and converted into Radon data. Next, the inverse Radon transformation is performed using the techniques described in U.S. patent application Ser. No. 07/631,818 and then a reconstructed image is generated and subsequently displayed.

It is therefore apparent that there has been provided in accordance with the present invention, a method and apparatus for generating Radon derivative data on a near uniformly spaced grid in a cone beam CT implementation that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

I claim:

1. A method of generating Radon derivative data on a substantially uniform polar grid, comprising the steps of:

providing a scanning trajectory about an object;

discretely sampling the scanning trajectory with a plurality of uniformly spaced cone beam source positions;

emitting cone beam energy from the discretely sampled cone beam source positions towards the object;

acquiring cone beam energy passing through the object on a detector as cone beam projection data;

partitioning the cone beam projection data into a plurality of vertical planes in Radon space, each vertical plane having a polar grid with a plurality of polar grid points uniformly spaced in r, $\theta$ and $\phi$ coordinates; and generating Radon derivative data on locations proximate to each of the plurality of polar grid points for each vertical plane.

2. A method according to claim 1, wherein the step of generating Radon derivative data comprises:

projecting the uniformly spaced cone beam source positions onto each of the plurality of vertical planes;

forming a band about a grid point P1 having coordinates ($r_i$, $\theta_j$, $\phi_k$) wherein the band has a width of $\Delta r$ and intersects the projected cone beam source positions;

determining whether the band contains a cone beam source position; and generating a hit for instances where the band contains a cone beam source position and a miss for instances where the band fails to contain a cone beam source position.

3. A method according to claim 2, further comprising the step of:

forming a first and second Radon circle about the grid point P1 ($r_i$, $\theta_j$, $\phi_k$) for a miss, wherein the first and second Radon circles are separated by $\delta\theta$ and have a point P2 with coordinates ($r_i$, $\theta_j$–$\delta\theta_1$, $\phi_k$) located on the first Radon circle and a point P3 with coordinates ($r_i$, $\theta_j$+$\delta_2$, $\phi_k$) located on the second Radon circle.

4. A method according to claim 3, further comprising the step of computing Radon derivative data for the point P2 with coordinates ($r_i$, $\theta_j$–$\delta\theta_1$, $\phi_k$) and the point P3 with coordinates ($r_1$, $\theta_j$+$\delta\theta_2$, $\phi_k$).

5. A method according to claim 4, further comprising the step of interpolating the Radon derivative data computed for the point P2 with coordinates ($r_i$, $\theta_j$–$\delta\theta_1$, $\phi_k$) and the point P3 with coordinates ($r_i$, $\theta_j$+$\delta\theta_2$, $\phi_k$) for the grid point P1 ($r_i$, $\theta_j$, $\phi_k$).

6. A method according to claim 3, further comprising the steps of:

shifting the band $\phi_k$–$\delta\phi1$ and $\phi_k$+$\delta\phi1$ for a miss;

determining whether the band contains a projected cone beam source beam positions in both the $\phi_k$–$\delta\phi1$ and $\phi_k$+$\delta\phi1$ direction; and generating a hit for instances where the band contains a cone beam source position.

7. A method according to claim 6, further comprising the step of computing Radon derivative data for hits in both the $\phi_k$– $\delta\phi1$ and $\phi_k$+$\delta\phi1$ direction.

8. A method according to claim 7, further comprising the step of interpolating Radon derivative data from the computed Radon derivative data.

9. An apparatus for generating Radon derivative data on a substantially uniform polar grid, comprising:

means for providing a scanning trajectory about an object;

means for discretely sampling the scanning trajectory with a plurality of uniformly spaced cone beam source positions;

means for emitting cone beam energy from the discretely sampled cone beam source positions towards the object;

means for acquiring cone beam energy passing through the object on a detector as cone beam projection data;

means for partitioning the cone beam projection data into a plurality of vertical planes in Radon space, each vertical plane having a polar grid with a plurality of polar grid points uniformly spaced in r, θ, and φ coordinates; and means for generating Radon derivative data on locations proximate to each of the plurality of polar grid points for each vertical plane.

10. An apparatus according to claim 9, wherein the Radon derivative data generating means comprises:

means for projecting the uniformly spaced cone beam source positions onto each of the plurality of vertical planes;

means for forming a band about a grid point P1 having coordinates $(r_i, \theta_j, \phi_k)$ wherein the band has a width of $\Delta r$ and intersects the projected cone beam source positions;

means for determining whether the band contains a cone beam source position; and means for generating a hit for instances where the band contains a cone beam source position and a miss for instances where the band fails to contain a cone beam source position.

11. An apparatus according to claim 10, further comprising:

means for forming a first and second Radon circle about the grid point P1 $(r_i, \theta_j, \phi_k)$ for a miss, wherein the first and second Radon circle are separated by $\delta\theta$ and have a point P2 with coordinates $(r_i, \theta_j-\delta\theta_1, \phi_k)$ located on the first Radon circle and a point P3 with coordinates $(r_i, \theta_j+\delta\theta_2, \phi_k)$ located on the second Radon circle.

12. An apparatus according to claim 11, further comprising means for computing Radon derivative data for the point P2 with coordinates $(r_i, \theta_j-\delta\theta_1, \phi_k)$ and the point P3 with coordinates $(r_i, \theta_j+\delta\theta_2, \phi_k)$.

13. An apparatus according to claim 12, further comprising means for interpolating Radon derivative data from the Radon derivative data computed for the point P2 with coordinates $(r_i, \theta_j-\delta\theta_1, \phi_k)$ and the point P3 with coordinates $(r_i, \theta_j+\delta\theta_2, \phi_k)$ for the point $(r_i, \theta_j, \phi_k)$.

14. An apparatus according to claim 11, further comprising:

means for shifting the band $\phi_k-\delta\phi 1$ and $\phi_k+\delta\phi 1$ for a miss;

means for determining whether the band contains a projected cone beam source beam positions in both the $\phi_k-\delta\phi 1$ and $\phi_k+\delta\phi 1$ direction; and means for generating a hit for instances where the band contains a cone beam source position.

15. An apparatus according to claim 14, further comprising means for computing Radon derivative data for hits in both the $\phi_k-\delta\phi 1$ and $\phi_k+\delta\phi 1$ direction.

16. An apparatus according to claim 15, further comprising means for interpolating Radon derivative data from the computed Radon derivative data.

\* \* \* \* \*